US009067953B2

(12) United States Patent
Scialdone

(10) Patent No.: US 9,067,953 B2
(45) Date of Patent: Jun. 30, 2015

(54) SYSTEMS FOR CARBON DIOXIDE AND SULFUR DIOXIDE REMOVAL

(75) Inventor: Mark A. Scialdone, West Grove, PA (US)

(73) Assignee: E I DU PONT DE NEMOURS AND COMPANY, Wilmington, DE (US)

(*) Notice: Subject to any disclaimer, the term of this patent is extended or adjusted under 35 U.S.C. 154(b) by 567 days.

(21) Appl. No.: 13/045,578

(22) Filed: Mar. 11, 2011

(65) Prior Publication Data
US 2011/0224427 A1 Sep. 15, 2011

Related U.S. Application Data

(60) Provisional application No. 61/313,173, filed on Mar. 12, 2010.

(51) Int. Cl.
C07D 235/28 (2006.01)
C07C 313/00 (2006.01)
C07F 7/08 (2006.01)
B01D 53/14 (2006.01)
C07C 335/38 (2006.01)
C07D 233/84 (2006.01)

(52) U.S. Cl.
CPC .......... C07F 7/0812 (2013.01); B01D 53/1475 (2013.01); B01D 53/1481 (2013.01); B01D 53/1493 (2013.01); B01D 2252/204 (2013.01); B01D 2252/2056 (2013.01); B01D 2252/30 (2013.01); C07C 335/38 (2013.01); C07D 233/84 (2013.01); C07D 235/28 (2013.01); Y02C 10/06 (2013.01)

(58) Field of Classification Search
None
See application file for complete search history.

(56) References Cited

U.S. PATENT DOCUMENTS

| | | | |
|---|---|---|---|
| 2,403,319 A | 7/1946 | Williams | |
| 4,095,962 A | 6/1978 | Richards | |
| 4,139,597 A | 2/1979 | Kohler | |
| 6,155,057 A | 12/2000 | Angell | |
| 6,579,343 B2 | 6/2003 | Brennecke et al. | |
| 7,157,588 B2 | 1/2007 | Harmer | |
| 7,208,605 B2 | 4/2007 | Davis | |
| 7,214,358 B2 | 5/2007 | Ravary | |
| 7,404,845 B2 | 7/2008 | Tempel | |
| 7,435,318 B2 | 10/2008 | Arlt | |
| 7,563,308 B2 | 7/2009 | Tempel | |
| 7,625,941 B2 | 12/2009 | Harmer | |
| 7,749,475 B2 | 7/2010 | Kim | |
| 8,119,818 B2 | 2/2012 | Foo | |
| 8,138,354 B2 | 3/2012 | Foo | |
| 8,202,446 B2 | 6/2012 | Tempel | |
| 8,313,558 B2 | 11/2012 | Shiflett | |
| 8,549,857 B2 | 10/2013 | Papile | |
| 2004/0035293 A1 | 2/2004 | Davis | |
| 2005/0129598 A1 | 6/2005 | Chinn et al. | |
| 2006/0197053 A1 | 9/2006 | Shiflett | |
| 2007/0028774 A1 | 2/2007 | Rochelle | |
| 2007/0131535 A1 | 6/2007 | Shiflett | |
| 2007/0264180 A1 | 11/2007 | Carrette | |
| 2008/0028777 A1 | 2/2008 | Boesmann | |
| 2008/0236390 A1 | 10/2008 | Anders et al. | |
| 2009/0235817 A1 | 9/2009 | Gu | |
| 2009/0293503 A1 | 12/2009 | Vandor | |
| 2010/0015040 A1 | 1/2010 | Kim | |
| 2010/0101231 A1 | 4/2010 | Westmeier | |
| 2010/0294131 A1 | 11/2010 | Bade | |
| 2011/0000221 A1 | 1/2011 | Minta | |
| 2011/0079017 A1 | 4/2011 | Gulen | |
| 2011/0105782 A1 | 5/2011 | Masi | |
| 2011/0203301 A1 | 8/2011 | Foo | |
| 2012/0312020 A1 | 12/2012 | Hume | |

FOREIGN PATENT DOCUMENTS

| | | |
|---|---|---|
| EP | 503910 | 9/1992 |
| JP | 09/000875 | 1/1997 |
| WO | WO 2007/012143 | 2/2007 |
| WO | WO 2007/073201 | 6/2007 |
| WO | 2008/122030 A1 | 10/2008 |
| WO | 2010/010238 A1 | 1/2010 |
| WO | 2010010239 A1 | 1/2010 |
| WO | WO 2010/010238 | 1/2010 |
| WO | WO 2010/010239 | 1/2010 |

OTHER PUBLICATIONS

Bates et al, "$CO_2$ Capture by a Task-Specific Ionic Liquid" Journal of the American Chemical Society vol. 124 No. 6, 2002, pp. 926-927.
Gutowski et al al "Amine-Functionalized Task-Specific Ionic Liquids: A Mechanistic Explanation for the Dramatic Increase in Viscosity Upon Complexation With $CO_2$ From Molecular Simulation", Journal of American Chemical Society 130: 14690-14704 (2008)..
Mark A. Scialdone, U.S. Appl. No. 13/045,820, filed Mar. 11, 2011.
Mark A Scialdone, U.S. Appl. No. 13/046,009, filed Mar. 11, 2011.
Mark A. Scialdone, U.S. Appl. No. 13/044,902, filed Mar. 10, 2011.
U.S. Appl. No. 12/0130088, filed May 24, 2012, Foo.
U.S. Appl. No. 11/0296993, filed Dec. 8, 2011, Foo.
U.S. Appl. No. 11/0223087, filed Sep. 15, 2011, Lustig.
U.S. Appl. No. 11/0223093, filed Sep. 15, 2011, Scialdone.
U.S. Appl. No. 11/0223085, filed Sep. 15, 2011, Kelkar.
U.S. Appl. No. 11/0220506, filed Sep. 15, 2011, Kelkar.
U.S. Appl. No. 11/0223086, filed Sep. 15, 2011, Scialdone.
U.S. Appl. No. 11/0296992, filed Dec. 8, 2011, Scialdone.
U.S. Appl. No. 11/0223084, filed Sep. 15, 2011, Scialdone.
U.S. Appl. No. 13/0269526, filed Oct. 17, 2013, Lustig.
Baldwin et al, Capturing $CO_2$: Gas Compression vs. Liquifaction, *Power Magazine*, Jun. 1, 2009, Online Print.
Enderby, Ionic Liquids: Recent Progress and Remaining Problems, 5 *J. Phys. Condens. Matter*, pp. B99-B106, 1993, IOP Publishing, London.
Karimi et al, Investigation of Intercooling Effect in $CO_2$ Capture Energy Consumption, 4 *Energy Procedia*, pp. 1601-1607, 2011, Elsivier, Online Print.
Romeo et al, Optimization of Intercooling Compression in $CO_2$ Capture Systems, 29 *Applied Thermal Engineering*, pp. 1744-1751, 2009, Elsivier, Online Print.
Scach et al, Exergoeconomic Analysis of Post Combustion $CO_2$ Capture Process, 20th European Symposium on Computer Aided Process Engineering, 2010, Elsivier, New York.
Welton, Room-Temperature Ionic Liquids—Solvents for Synthesis and Catalysis, 99 *Chem. Rev.* 2071-2083, Jul. 7, 1999, Online Print.

Primary Examiner — Noble Jarrell

(57) ABSTRACT

This invention relates to sulfur based compounds useful in methods of carbon dioxide or sulfur dioxide removal.

4 Claims, 1 Drawing Sheet

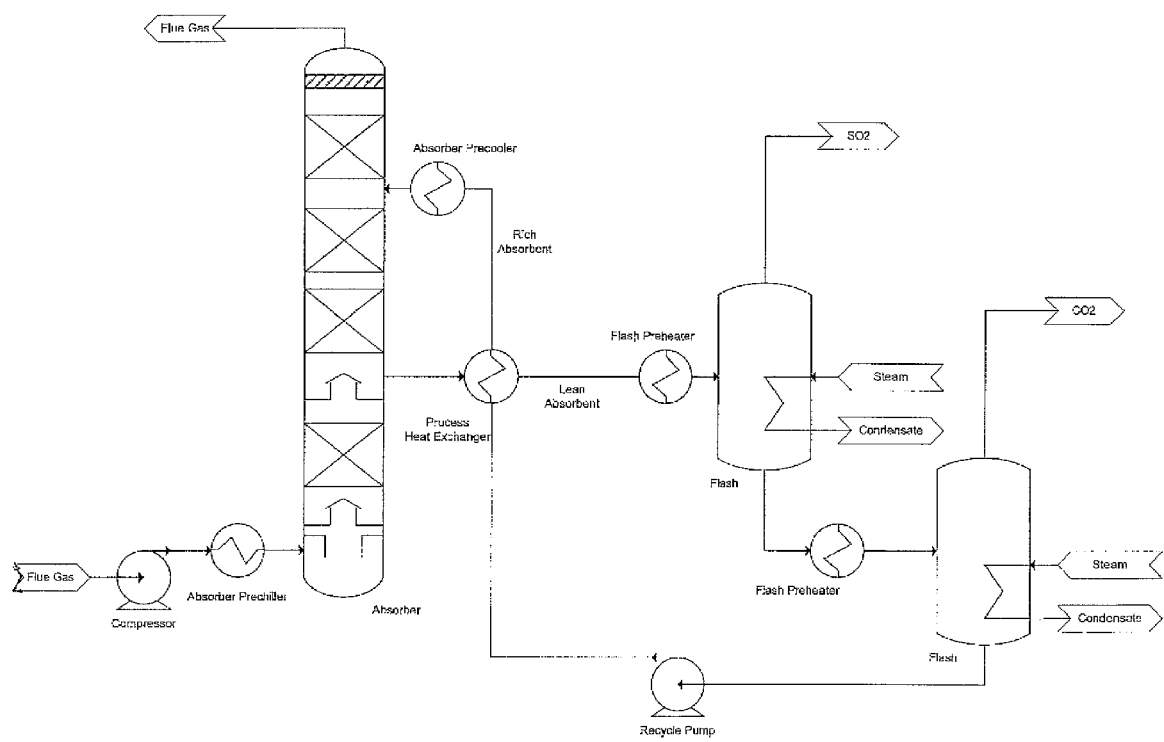

SYSTEMS FOR CARBON DIOXIDE AND SULFUR DIOXIDE REMOVAL

This application claims priority under 35 U.S.C. §119(e) from, and claims the benefit of, U.S. Provisional Application No. 61/313,173, filed Mar. 12, 2010, which is by this reference incorporated in its entirety as a part hereof for all purposes.

TECHNICAL FIELD

This invention relates to the removal of carbon dioxide and/or sulfur dioxide from a gaseous mixture.

BACKGROUND

There is increasing interest in methods to reduce or capture $CO_2$ from many different gaseous mixtures. $CO_2$ is an undesired component that is present in many gas streams such as natural gas and effluent gases, and there is also much global interest in reducing $CO_2$ emissions from combustion exhaust for the prevention of global warming. $CO_2$ can be removed or captured by many means, such as physical or chemical absorption of the gas by a liquid or solid.

Currently, a common method of carbon dioxide capture from process streams in industrial complexes involves the use of aqueous solutions of alkanolamines, but usually on a small scale. The process has been used commercially since the early 1930s (see, for example, Kohl and Nielsen, Gas Purification, 5th Edition, Gulf Publishing, Houston Tex., 1997), and is based on the reaction of a weak base (alkanolamine) with a weak acid ($CO_2$) to produce a water-soluble salt. This reaction is reversible, and the equilibrium is temperature dependent.

The use of alkanolamines as absorbents for $CO_2$ (from power plant flue gases, for example) is somewhat disadvantaged in respect of the amount of energy needed to regenerate the $CO_2$-rich solvent, the size of the $CO_2$ capture plant, and the loss of alkanolamines to the environment. Among conventional alkanolamines, monoethanolamine (MEA) is considered an attractive solvent at low partial pressures of $CO_2$ because it reacts at a rapid rate and the cost of the raw materials is low compared to that of secondary and tertiary amines. The costs of absorption processes using MEA are high, however, because of the high energy consumption in regeneration, and because of operation problems such as corrosion, solvent loss and solvent degradation. Furthermore, MEA can be loaded up to only 0.5 mol of $CO_2$/mol of MEA, or 33 mol %, as a result of the stable carbonates formed.

Physical absorption systems have advantages over chemical absorption such as lower energy costs, but also have disadvantages such as solvent losses and low $CO_2$ capacity. A need thus remains for systems and materials capable of providing low-cost, high-capacity methods of $CO_2$ capture.

Concurrently, there is also interest in methods to reduce or capture $SO_2$ from many different gaseous mixtures. Ideally the same process and compounds could be used for both gases, with the capability to selectively release the gases upon demand.

SUMMARY

Provided is a composition as represented by the structure of the following Formula IA, Formula IIA, or Formula IIIA:

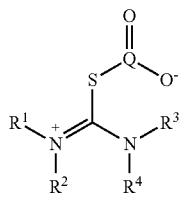

Formula IA

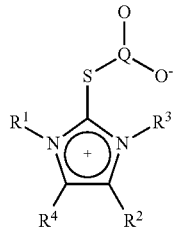

Formula IIA

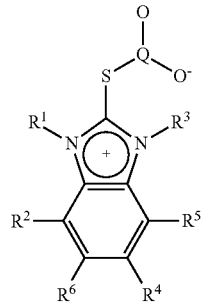

Formula IIIA wherein
1) $R^1, R^2, R^3, R^4, R^5$, and $R^6$ are independently selected from the group consisting of:
   i) H,
   ii) halogen such as Cl, Br, F, I,
   iii) —$CH_3$, —$C_2H_5$, or $C_3$ to $C_{25}$ straight-chain, branched or cyclic alkane or alkene, optionally substituted with at least one member selected from the group consisting of Cl, Br, F, I, OH, $NH_2$ and SH;
   iv) —$CH_3$, —$C_2H_5$, or $C_3$ to $C_{25}$ straight-chain, branched or cyclic alkane or alkene comprising one to three heteroatoms selected from the group consisting of O, N, Si and S, and optionally substituted with at least one member selected from the group consisting of Cl, Br, F, I, OH, $NH_2$ and SH;
   v) $C_6$ to $C_{20}$ unsubstituted aryl, or $C_6$ to $C_{25}$ unsubstituted heteroaryl having one to three heteroatoms independently selected from the group consisting of O, N, Si and S;
   vi) $C_6$ to $C_{25}$ substituted aryl, or $C_6$ to $C_{25}$ substituted heteroaryl having one to three heteroatoms independently selected from the group consisting of O, N, Si and S; and wherein said substituted aryl or substituted heteroaryl has one to three substituents independently selected from the group consisting of:
      (A) —$CH_3$, —$C_2H_5$, or $C_3$ to $C_{25}$ straight-chain, branched or cyclic alkane or alkene, optionally substituted with at least one member selected from the group consisting of Cl, Br, F, I, OH, $NH_2$ and SH, (B) OH,
(C) NH$_2$, and
(D) SH; and vii) —(CH$_2$)$_n$Si(CH$_2$)$_m$CH$_3$, —(CH$_2$)$_n$Si(CH$_3$)$_3$, or —(CH$_2$)$_n$OSi(CH$_3$)$_m$, where n is independently 1-4 and m is independently 0-4;

wherein any of R$^1$, R$^2$, R$^3$, R$^4$, R$^5$, and R$^6$ can together form a ring; and 2) Q is S or C.

This invention also provides a method of generating a compound as represented by the structure of the Formula I, II or III, or a mixture thereof, by heating a composition as represented by the structure of the Formula IA, IIA or IIIA, or mixture thereof, and/or by contacting the composition as represented by the structure of the Formula IA, IIA or IIIA, or mixture thereof, with a non-solvent to separate a compound as represented by the structure of the Formula I, II or III, or a mixture thereof, and recovering the compound as represented by the structure of the Formula I, II or III, or a mixture thereof.

This invention also provides a method of generating CO$_2$ and/or SO$_2$ by heating a composition as represented by the structure of the Formula IA, IIA or IIIA, or mixture thereof, and/or by contacting the composition as represented by the structure of the Formula IA, IIA or IIIA, or mixture thereof, with a non-solvent to separate CO$_2$ and/or SO$_2$, and recovering CO$_2$ and/or SO$_2$.

FIGURES

FIG. 1 is a drawing of a process that can be used to selectively absorb and release SO$_2$ and CO$_2$ from a gaseous mixture.

DETAILED DESCRIPTION

In the description of the compositions hereof, the following definitional structure is provided for certain terminology as employed variously in the specification:

An "alkyl" group is a monovalent (i.e. having a valence of one) group having the Formula C$_n$H$_{2n+1}$.

An "aryl" means a group defined as a monovalent radical formed by removal of a hydrogen atom from a hydrocarbon that is structurally composed entirely of one or more benzene rings.

A "heteroaryl" refers to unsaturated rings of 6 atoms containing one or two O and S atoms and/or one to four N atoms provided that the total number of hetero atoms in the ring is 4 or less, or bicyclic rings wherein a five or six membered ring containing O, S, and N atoms as defined above is fused to a benzene or pyridyl ring.

CO$_2$ and SO$_2$ Absorption

In one embodiment hereof, there are provided methods for removal of one or more of CO$_2$ and SO$_2$ from a gaseous mixture in which they are contained. The compounds described herein are thus useful for separation methods such as CO$_2$ and/or SO$_2$ absorption, adsorption, or other types of recovery. This can be accomplished by contacting a gaseous mixture containing one or more of CO$_2$ and SO$_2$ with one or more of the compounds represented by Formula I, Formula II, or Formula III:

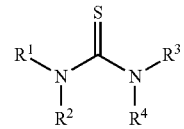

Formula I

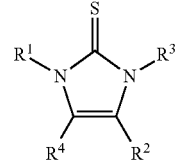

Formula II

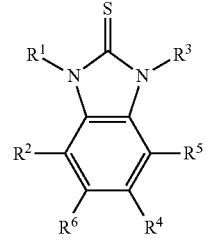

Formula III wherein
2) R$^1$, R$^2$, R$^3$, R$^4$, R$^5$, and R$^6$ are independently selected from the group consisting of:
i) H,
ii) halogen,
iii) —CH$_3$, —C$_2$H$_5$, or C$_3$ to C$_{25}$ straight-chain, branched or cyclic alkane or alkene, optionally substituted with at least one member selected from the group consisting of Cl, Br, F, I, OH, NH$_2$ and SH;
iv) —CH$_3$, —C$_2$H$_5$, or C$_3$ to C$_{25}$ straight-chain, branched or cyclic alkane or alkene comprising one to three heteroatoms selected from the group consisting of O, N, Si and S, and optionally substituted with at least one member selected from the group consisting of Cl, Br, F, I, OH, NH$_2$ and SH;
v) C$_6$ to C$_{20}$ unsubstituted aryl, or C$_6$ to C$_{25}$ unsubstituted heteroaryl having one to three heteroatoms independently selected from the group consisting of O, N, Si and S;
vi) C$_6$ to C$_{25}$ substituted aryl, or C$_6$ to C$_{25}$ substituted heteroaryl having one to three heteroatoms independently selected from the group consisting of O, N, Si and S; and wherein said substituted aryl or substituted heteroaryl has one to three substituents independently selected from the group consisting of:
(A) —CH$_3$, —C$_2$H$_5$, or C$_3$ to C$_{25}$ straight-chain, branched or cyclic alkane or alkene, optionally substituted with at least one member selected from the group consisting of Cl, Br, F, I, OH, NH$_2$ and SH,
(B) OH,
(C) NH$_2$, and
(D) SH; and vii) —(CH$_2$)$_n$Si(CH$_2$)$_m$CH$_3$, —(CH$_2$)$_n$Si(CH$_3$)$_3$, or —(CH$_2$)$_n$OSi(CH$_3$)$_m$, where n is independently 1-4 and m is independently 0-4; and wherein any of R$^1$, R$^2$, R$^3$, R$^4$, R$^5$, and R$^6$ can together form a ring.

In one embodiment, in Formula II R$^1$ is an electron rich (e.g. negatively charged) aryl group, R$^2$ is a C$_1$~C$_{10}$, C$_1$~C$_8$, or C$_1$~C$_6$, alkyl group, R$^3$ is H or an electron withdrawing (electron deficient e.g. positively charged) group, and R$^4$ is a long chain (C$_1$~C$_{20}$) alkyl group. In another embodiment in Formula I and Formula III $R^1$ is an electron rich (e.g. negatively charged) aryl group, $R^2$ is H or an electron withdrawing (electron deficient e.g. positively charged) group, and $R^2$, $R^4$, $R^5$, and $R^6$ are independently H, an alkyl group, or an aryl group.

Substituted thioureas may be prepared using the method described by Neville et al. (*Org. Syn. Coll.* 5:801, 1973). For example, a solution of cyclohexylamine in anhydrous benzene is added to silicon tetraisocyanate in anhydrous benzene. The mixture is heated and the benzene is removed; isopropyl alcohol is added to the residue, and the mixture is heated and filtered.

1,3-diakylimidazole-2-thiones and benzoimidazole thiones may be prepared by thionation of imidazolium halides, as described by Benac et al. (*Org. Syn. Coll.* 7:195, 1990). For example, 1,3-dimethylimidazolium iodide, anhydrous potassium carbonate, sulfur and methanol are combined. The mixture is stirred, filtered, washed with dichloromethane and dried.

Without wishing to be bound by theory, it is believed that the $CO_2$ and $SO_2$ are separated from the gaseous mixture by binding to the nucleophilic compounds of Formula I, II and III to form a thiocarbonate or thiobisulfite, as illustrated below for compounds of Formula II and carbon dioxide:

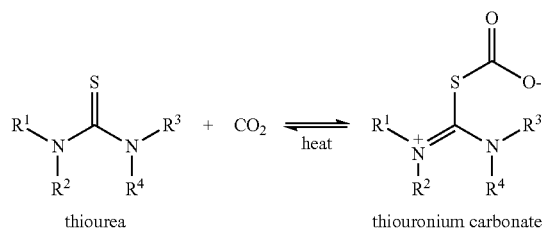

thiourea          thiouronium carbonate

Upon heating, the carbon dioxide and sulfur dioxide can be released. One advantage of the present method is that due to the differences in bond strength, the sulfur dioxide and carbon dioxide can be released at different temperatures. This process is illustrated below:

mizing surface area contact are desirable. The conditions at which the process are conducted vary according to the compounds of the gaseous stream, the partial pressure of the $CO_2$ and/or $SO_2$, and equipment used, but in suitable embodiments be at temperatures ranging from ambient to about 200° C., and at pressures ranging from 1-5 atmospheres.

Illustratively, contacting the compounds of Formula I, Formula II, or Formula III with a gaseous mixture can be performed by use of conventional liquid absorbers, such as counter-current liquid absorbers or cyclone scrubbers, by permeation through a supported liquid membrane, or by use of a fixed bed.

In one embodiment hereof, a liquid solvent can be used to remove a compound from a gas stream in an absorber, where gas and liquid are brought into contact countercurrently, and the gas is dissolved into the solvent. The absorber is typically equipped with trays or packing to provide a large liquid-gas contact area. Valve and sieve trays may be used, as may bubble cap and tunnel trays, where a tray typically has overflow weirs and downcorners to create hydrostatic holdup of the downward flow of the liquid. Random packings can also be used such as Rashig rings, Pall rings or Berl saddles, or structured packings of woven or nonwoven fabrics of metal, synthetic materials or ceramics.

The purified gas is taken off the head of the column. The solvent laden with the absorbed compound is withdrawn from the bottom of the absorber, routed to a regeneration system where it is freed of absorbed the absorbed gas component, and returned as lean solvent to the absorber. Regeneration may be accomplished by flash regeneration, which can involve pressure reduction and mild reboiling in one or more stages; by inert gas stripping; or by high temperature reboiling wherein the solvent is stripped by its own vapor, which is then condensed from the overhead gas and recycled as reflux.

In an absorber, a batch process may be performed where the flow rate through the vessel correlates to the residence time of contact and is suitably chosen to afford an effluent stream with the desired purification tolerance. To promote the desired intimate mixing, such gas/liquid absorption units also may be operated in a dual flow mode. Such dual flow can be

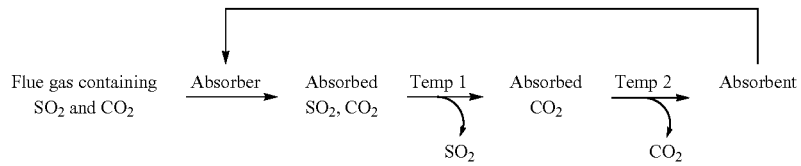

The gaseous mixture containing $CO_2$ and/or $SO_2$ can be any mixture of which $CO_2$ and/or $SO_2$ is a constituent part, or can be 100% $CO_2$, 100% $SO_2$, or any combination of $CO_2$ and $SO_2$. Examples of gaseous mixtures containing $CO_2$ and/or $SO_2$ include without limitation flue gases, combustion exhausts, natural gas streams, streams from rebreathing apparatus, and the products of chemical synthesis, degradation or fermentation operations. The gases and gaseous mixtures referred to herein may include vapors (volatilized liquids), gaseous compounds and/or other gaseous elements.

Contacting the compounds of Formula I, Formula II, or Formula III with a gaseous mixture containing $CO_2$ and/or $SO_2$ may be accomplished by any means that promotes intimate mixing of the compounds of Formula I with the source gas and is conducted for a time sufficient to allow significant removal of the targeted component(s). Thus, systems maxico-current or counter-current. In such an embodiment, the gas mixture and the ionic liquid(s) flow through a purification unit contemporaneously. Methods for carbon dioxide absorption are further discussed in U.S. Pat. No. 6,579,343; U.S. Ser. No. 05/129,598; and US 2008/0236390 (each of which is by this reference incorporated as a part hereof for all purposes).

Where supported liquid membranes are used for gas recovery, the membrane may include a solvent such as an ionic liquid contained within the pores of a solid microporous support, such as a ceramic, metal, or polymeric support. Supported liquid membranes fabricated from supports such as ceramics, metals, and certain heat stable polymers may advantageously be used in higher than ambient temperature operations. Such higher temperature operations may be preferred to effect a more rapid separation, requiring less contact time. In addition, these higher temperature operations may also be a consequence of the process configuration, such as configurations requiring purification of high temperature exhaust gases or other gases exiting high temperature operations. Supported liquid membranes suitable for purifying high temperature gases obviate the need to pre-cool such gases before contact with the supported liquid membrane. The supported liquid membranes may be fabricated as thin films or hollow fibers with continuous networks of interconnected pores leading from one surface to the other. Supported liquid membranes contact a feed gas mixture on one side of the membrane and may effect separation of a gas component from the mixture by allowing that component to escape via permeation or diffusion into the compounds of Formula I, Formula II, or Formula III and through the liquid membrane.

The compounds of Formula I, Formula II, or Formula III can also be used in a conventional gas/liquid absorption unit-based system comprising a fixed bed. Such systems can be operated in batch mode or continuous flow mode. In a typical batch mode configuration, the compounds are introduced into a vessel followed by introduction of the gas mixture. After a prescribed residence time, the resulting gas is removed, leaving behind an impurity or group of impurities dissolved in the compounds of Formula I, Formula II, or Formula III. The batch purified gas can be generated by heating or reduced pressure treatment as described above. To maximize contact of compound and the gas mixture, the compounds of Formula I, Formula II, or Formula III can be coated on a solid support, such as glass beads, and the like, to increase the surface area of the compounds of Formula I, Formula II, or Formula III capable of contacting the gas mixture.

In one embodiment, this invention provides a method wherein the removal of $CO_2$ and/or $SO_2$ from a gaseous mixture occurs in a removal apparatus; wherein, in the removal apparatus, $CO_2$ and/or $SO_2$ is dissolved into compounds of Formula I, Formula II, or Formula III to form (i) a purified fraction that is depleted in $CO_2$ and/or $SO_2$ content (compared to the content thereof in the original feed of the gaseous mixture) and (ii) a solvent fraction that is enriched in $CO_2$ and/or $SO_2$ content (compared to the content thereof in the original feed of the gaseous mixture); and wherein the solvent fraction is separated from the removal apparatus. In a further alternative embodiment of the methods hereof, $CO_2$ and/or $SO_2$ can be separated from the solvent fraction to form a rectified solvent fraction, and the rectified solvent fraction can be returned to the removal apparatus.

Equipment and processes that can be used for the absorption of $CO_2$ and/or $SO_2$ are further described in Absorption, *Ullmann's Encyclopedia of Industrial Chemistry* [2002, (Wiley-VCH Verlag GmbH & Co. KGa) Johann Schlauer and Manfred Kriebel, Jun. 15, 2000 (DOI: 10.1002/14356007.b03_08)]; and Absorption, *Kirk-Othmer Encyclopedia of Chemical Technology* [2003, (John Wiley & Sons, Inc), Manuel Laso and Urs von Stockar (DOI:10.1002/0471238961.0102191519201503.a01.pub2)]. One embodiment of apparatus that can be used to selectively absorb and release $CO_2$ and $SO_2$ from the same gaseous mixture is shown in FIG. 1.

Additives

Various additives may be used to enhance the absorption of $CO_2$ and/or $SO_2$ by the compounds described herein. One class of additives is ionic liquids. Ionic liquids suitable for use herein comprise an anion and a cation, the cation is selected from the group consisting of cations represented by the structures of the following formulae:

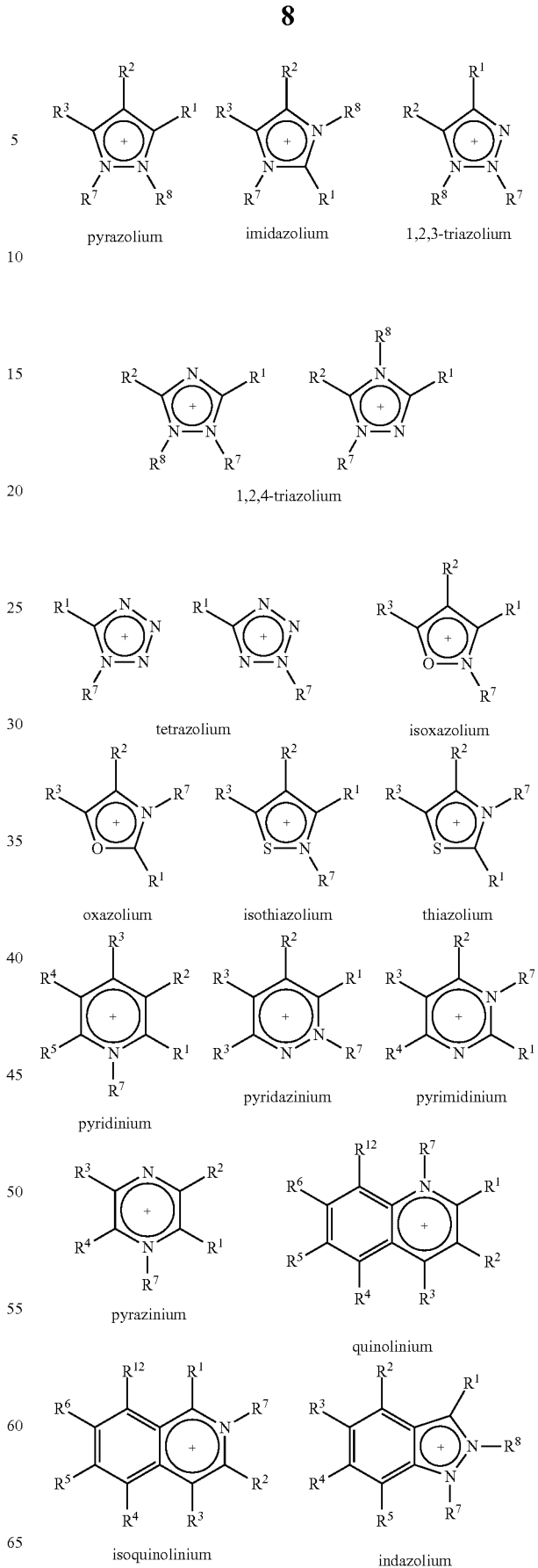

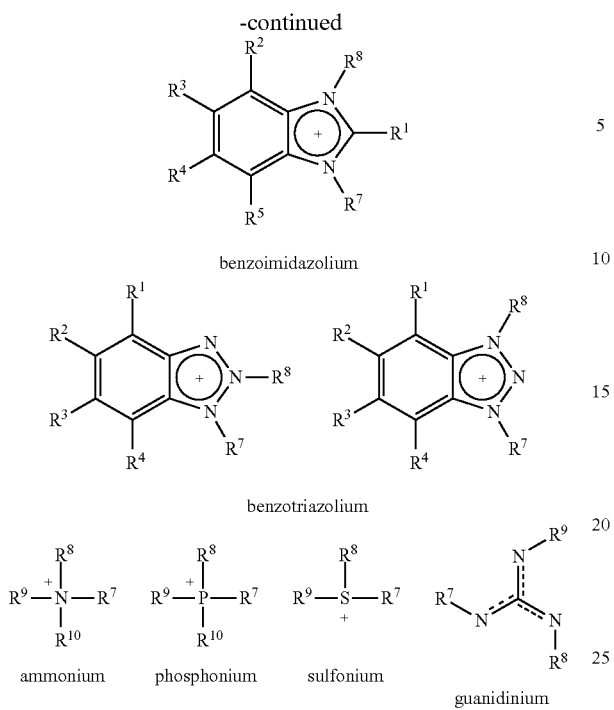

benzoimidazolium benzotriazolium ammonium    phosphonium    sulfonium    guanidinium wherein:
a) $R^1$, $R^2$, $R^3$, $R^4$, $R^5$, $R^6$, and $R^{12}$ are independently selected from the group consisting of:
(i) H,
(ii) halogen such as Cl, Br, F, I,
(iii) —$CH_3$, —$C_2H_5$, or $C_3$ to $C_{25}$ straight-chain, branched or cyclic alkane or alkene, optionally substituted with at least one member selected from the group consisting of Cl, Br, F, I, OH, $NH_2$ and SH;
(iv) —$CH_3$, —$C_2H_5$, or $C_3$ to $C_{25}$ straight-chain, branched or cyclic alkane or alkene comprising one to three heteroatoms selected from the group consisting of O, N, Si and S, and optionally substituted with at least one member selected from the group consisting of Cl, Br, F, I, OH, $NH_2$ and SH;
(v) $C_6$ to $C_{20}$ unsubstituted aryl, or $C_6$ to $C_{25}$ unsubstituted heteroaryl having one to three heteroatoms independently selected from the group consisting of O, N, Si and S;
(vi) $C_6$ to $C_{25}$ substituted aryl, or $C_6$ to $C_{25}$ substituted heteroaryl having one to three heteroatoms independently selected from the group consisting of O, N, Si and S; and wherein said substituted aryl or substituted heteroaryl has one to three substituents independently selected from the group consisting of:
(A) —$CH_3$, —$C_2H_5$, or $C_3$ to $C_{25}$ straight-chain, branched or cyclic alkane or alkene, optionally substituted with at least one member selected from the group consisting of Cl, Br, F, I, OH, $NH_2$ and SH,
(B) OH,
(C) $NH_2$, and
(D) SH;
(vii) —$(CH_2)_nSi(CH_2)_mCH_3$, —$(CH_2)_nSi(CH_3)_3$, or —$(CH_2)_nOSi(CH_3)_m$, where n is independently 1-4 and m is independently 0-4;
b) $R^7$, $R^8$, $R^9$, and $R^{10}$ are independently selected from the group consisting of:
(ix) —$CH_3$, —$C_2H_5$, or $C_3$ to $C_{25}$ straight-chain, branched or cyclic alkane or alkene, optionally substituted with at least one member selected from the group consisting of Cl, Br, F, I, OH, $NH_2$ and SH;
(x) —$CH_3$, —$C_2H_5$, or $C_3$ to $C_{25}$ straight-chain, branched or cyclic alkane or alkene comprising one to three heteroatoms selected from the group consisting of O, N, Si and S, and optionally substituted with at least one member selected from the group consisting of Cl, Br, F, I, OH, $NH_2$ and SH;
(xi) $C_6$ to $C_{25}$ unsubstituted aryl, or $C_6$ to $C_{25}$ unsubstituted heteroaryl having one to three heteroatoms independently selected from the group consisting of O, N, Si and S; and
(xii) $C_6$ to $C_{25}$ substituted aryl, or $C_6$ to $C_{25}$ substituted heteroaryl having one to three heteroatoms independently selected from the group consisting of O, N, Si and S; and wherein said substituted aryl or substituted heteroaryl has one to three substituents independently selected from the group consisting of:
(E) —$CH_3$, —$C_2H_5$, or $C_1$ to $C_{25}$ straight-chain, branched or cyclic alkane or alkene, optionally substituted with at least one member selected from the group consisting of Cl, Br, F, I, OH, $NH_2$ and SH,
(F) OH,
(G) $NH_2$, and
(H) SH;
(xiii) —$(CH_2)_nSi(CH_2)_mCH_3$, —$(CH_2)_nSi(CH_3)_3$, or —$(CH_2)_nOSi(CH_3)_m$, where n is independently 1-4 and m is independently 0-4; and
c) optionally at least two of $R^1$, $R^2$, $R^3$, $R^4$, $R^5$, $R^6$, $R^7$, $R^8$, $R^9$, and $R^{10}$ can together form a cyclic or bicyclic alkanyl or alkenyl group.

In one embodiment, the ionic liquid comprises an anion selected from one or more members of the group consisting of: $[CH_3CO_2]^-$, $[HSO_4]^-$, $[CH_3OSO_3]^-$, $[C_2H_5OSO_3]^-$, $[AlCl_4]^-$, $[CO_3]^{2-}$, $[HCO_3]^-$, $[NO_2]^-$, $[NO_3]^-$, $[SO_4]^{2-}$, $[PO_3]^{3-}$, $[HPO_3]^{2-}$, $[H_2PO_3]^{1-}$, $[PO_4]^{3-}$, $[HPO_4]^{2-}$, $[H_2PO_4]^-$, $[HSO_3]^-$, $[CuCl_2]^-$, $Cl^-$, $Br^-$, $I^-$, $SCN^-$, and a fluorinated anion.

In one embodiment, the ionic liquid comprises a cation selected from one or more members of the group consisting of pyridinium, pyridazinium, pyrimidinium, pyrazinium, imidazolium, pyrazolium, thiazolium, oxazolium, triazolium, phosphonium, ammonium, and guanidinium.

In another embodiment, the ionic liquid comprises an anion selected from one or more members of the group consisting of aminoacetate, ascorbate, benzoate, catecholate, citrate, dimethylphosphate, formate, fumarate, gallate, glycolate, glyoxylate, iminodiacetate, isobutyrate, kojate, lactate, levulinate, oxalate, pivalate, propionate, pyruvate, salicylate, succinamate, succinate, tiglate, tetrafluoroborate, tetrafluoroethanesulfonate, tropolonate, $[CH_3CO_2]^-$, $[HSO_4]^-$, $[CH_3OSO_3]^-$, $[C_2H_5OSO_3]^-$, $[AlCl_4]^-$, $[CO_3]^{2-}$, $[HCO_3]^-$, $[NO_2]^-$, $[NO_3]^-$, $[SO_4]^{2-}$, $[PO_4]^{3-}$, $[HPO_4]^{2-}$, $[H_2PO_4]^-$, $[HSO_3]^-$, $[CuCl_2]^-$, $Cl^-$, $Br^-$, $I^-$, $SCN^-$, $[BF_4]^-$, $[PF_6]^-$, $[SbF_6]^-$, $[CF_3SO_3]^-$, $[HCF_2CF_2SO_3]^-$, $[CF_3HFCCF_2SO_3]^-$, $[HCClFCF_2SO_3]^-$, $[(CF_3SO_2)_2N]^-$, $[(CF_3CF_2SO_2)_2N]^-$, $[(CF_3SO_2)_3C]^-$, $[CF_3CO_2]^-$, $[CF_3OCFHCF_2SO_3]^-$, $[CF_3CF_2OCFHCF_2SO_3]^-$, $[CF_3CFHOCF_2CF_2SO_3]^-$, $[CF_2HCF_2OCF_2CF_2SO_3]^-$, $[CF_2ICF_2OCF_2CF_2SO_3]$, $[CF_3CF_2OCF_2CF_2SO_3]^-$, $[(CF_2HCF_2SO_2)_2N]^-$, $[(CF_3CFHCF_2SO_2)_2N]^-$, $F^-$, and anions represented by the structure of the following formula:

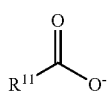

wherein $R^{11}$ is selected from the group consisting of:
(i) —$CH_3$, —$C_2H_5$, or $C_3$ to $C_{17}$ straight-chain, branched or cyclic alkane or alkene, optionally substituted with at least one member selected from the group consisting of Cl, Br, F, I, OH, $NH_2$ and SH;
(ii) —$CH_3$, —$C_2H_5$, or $C_3$ to $C_{10}$ straight-chain, branched or cyclic alkane or alkene comprising one to three heteroatoms selected from the group consisting of O, N, Si and S, and optionally substituted with at least one member selected from the group consisting of Cl, Br, F, I, OH, $NH_2$ and SH;
(iii) $C_6$ to $C_{10}$ unsubstituted aryl, or $C_6$ to $C_{10}$ unsubstituted heteroaryl having one to three heteroatoms independently selected from the group consisting of O, N, Si and S; and
(iv) $C_6$ to $C_{10}$ substituted aryl, or $C_6$ to $C_{10}$ substituted heteroaryl having one to three heteroatoms independently selected from the group consisting of O, N, Si and S; and wherein said substituted aryl or substituted heteroaryl has one to three substituents independently selected from the group consisting of:
(A) —$CH_3$, —$C_2H_5$, or $C_3$ to $C_{10}$ straight-chain, branched or cyclic alkane or alkene, optionally substituted with at least one member selected from the group consisting of Cl, Br, F, I, OH, $NH_2$ and SH,
(B) OH,
(C) $NH_2$, and
(D) SH.

Compositions

Also described herein are the compositions as represented by the structure of the following Formula IA, Formula IIA, and Formula IIIA:

Formula IA

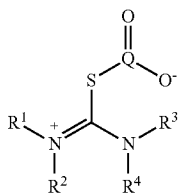

Formula IIA

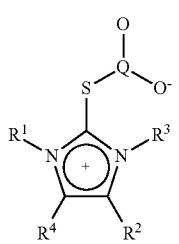

Formula IIIA

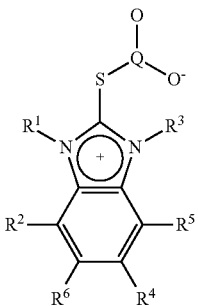

wherein
3) $R^1$, $R^2$, $R^3$, $R^4$, $R^5$, and $R^6$ are independently selected from the group consisting of:
i) H,
ii) halogen such as Cl, Br, F, I,
iii) —$CH_3$, —$C_2H_5$, or $C_3$ to $C_{25}$ straight-chain, branched or cyclic alkane or alkene, optionally substituted with at least one member selected from the group consisting of Cl, Br, F, I, OH, $NH_2$ and SH;
iv) —$CH_3$, —$C_2H_5$, or $C_3$ to $C_{25}$ straight-chain, branched or cyclic alkane or alkene comprising one to three heteroatoms selected from the group consisting of O, N, Si and S, and optionally substituted with at least one member selected from the group consisting of Cl, Br, F, I, OH, $NH_2$ and SH;
v) $C_6$ to $C_{20}$ unsubstituted aryl, or $C_6$ to $C_{25}$ unsubstituted heteroaryl having one to three heteroatoms independently selected from the group consisting of O, N, Si and S;
vi) $C_6$ to $C_{25}$ substituted aryl, or $C_6$ to $C_{25}$ substituted heteroaryl having one to three heteroatoms independently selected from the group consisting of O, N, Si and S; and wherein said substituted aryl or substituted heteroaryl has one to three substituents independently selected from the group consisting of:
(A) —$CH_3$, —$C_2H_5$, or $C_3$ to $C_{25}$ straight-chain, branched or cyclic alkane or alkene, optionally substituted with at least one member selected from the group consisting of Cl, Br, F, I, OH, $NH_2$ and SH,
(B) OH,
(C) $NH_2$, and
(D) SH; and
vii) —$(CH_2)_nSi(CH_2)_mCH_3$, —$(CH_2)_nSi(CH_3)_3$, or —$(CH_2)_nOSi(CH_3)_m$, where n is independently 1-4 and m is independently 0-4;
wherein any of $R^1$, $R^2$, $R^3$, $R^4$, $R^5$, and $R^6$ can together form a ring; and
2) Q is S or C.

In one embodiment, in Formula IA $R^1$ is an electron rich (e.g. negatively charged) aryl group, $R^2$ is a $C_1$~$C_{10}$, $C_1$~$C_8$, or $C_1$~$C_6$, alkyl group, $R^3$ is H or an electron withdrawing (electron deficient e.g. positively charged) group, and $R^4$ is a long chain ($C_1$~$C_{20}$) alkyl group. In another embodiment, in Formula IIA and Formula IIIA $R^1$ is an electron rich (e.g. negatively charged) aryl group, $R^2$ is H or an electron withdrawing (electron deficient e.g. positively charged) group, and $R^2$, $R^4$, $R^5$, and $R^6$ are independently H, an alkyl group, or an aryl group. In yet another embodiment Q is C.

The compositions of Formula IA, IIA, and IIIA can be prepared by the reaction of compounds of Formula I, II and III with $CO_2$ and/or $SO_2$, as described above. The compositions of Formula IA, IIA, and IIIA find utility in their use, for example, as a source of either or both of (i) the compounds of Formula I, II and III, and (ii) $CO_2$ and $SO_2$.

In particular, the compositions of Formula IA, IIA, and IIIA may be used in either of the following methods A method of generating a compound as represented by the structure of the Formula I, II or III, or a mixture thereof, by heating a composition as represented by the structure of the Formula IA, IIA or IIIA, or mixture thereof, and/or by contacting the composition as represented by the structure of the Formula IA, IIA or IIIA, or mixture thereof, with a non-solvent to separate a compound as represented by the structure of the Formula I, II or III, or a mixture thereof, and recovering the compound as represented by the structure of the Formula I, II or III, or a mixture thereof.

A method of generating $CO_2$ and/or $SO_2$ by heating a composition as represented by the structure of the Formula IA, IIA or IIIA, or mixture thereof, and/or by contacting the composition as represented by the structure of the Formula IA, IIA or IIIA, or mixture thereof, with a non-solvent to separate $CO_2$ and/or $SO_2$, and recovering $CO_2$ and/or $SO_2$.

Various materials suitable for use herein may be made by processes known in the art, and/or are available commercially from suppliers such as Alfa Aesar (Ward Hill, Mass.), City Chemical (West Haven, Conn.), Fisher Scientific (Fairlawn, N.J.), Sigma-Aldrich (St. Louis, Mo.) or Stanford Materials (Aliso Viejo, Calif.).

Where a range of numerical values is recited or established herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges was explicitly recited. Where a range of numerical values is stated herein as being greater than a stated value, the range is nevertheless finite and is bounded on its upper end by a value that is operable within the context of the invention as described herein. Where a range of numerical values is stated herein as being less than a stated value, the range is nevertheless bounded on its lower end by a non-zero value.

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the subject matter hereof, however, may be stated or described as consisting essentially of certain features or elements, in which embodiment features or elements that would materially alter the principle of operation or the distinguishing characteristics of the embodiment are not present therein. A further alternative embodiment of the subject matter hereof may be stated or described as consisting of certain features or elements, in which embodiment, or in insubstantial variations thereof, only the features or elements specifically stated or described are present.

In the various embodiments of this invention, an ionic compound formed by selecting any of the individual cations described or disclosed herein, and by selecting any of the individual anions described or disclosed herein, may be used for the purposes hereof. Correspondingly, in yet other embodiments, a subgroup of ionic liquids formed by selecting (i) a subgroup of any size of cations, taken from the total group of cations described and disclosed herein in all the various different combinations of the individual members of that total group, and (ii) a subgroup of any size of anions, taken from the total group of anions described and disclosed herein in all the various different combinations of the individual members of that total group, may be used for the purposes hereof. In forming an ionic compound, or a subgroup of ionic compounds, by making selections as aforesaid, the ionic compound or subgroup will be identified by, and used in, the absence of the members of the group of cations and/or the group of anions that are omitted from the total group thereof to make the selection; and, if desirable, the selection may thus be made in terms of the members of one or both of the total groups that are omitted from use rather than the members of the group (s) that are included for use.

Each of the formulae shown herein describes each and all of the separate, individual compounds and compositions that can be assembled in that formula by (1) selection from within the prescribed range for one of the variable radicals, substituents or numerical coefficents while all of the other variable radicals, substituents or numerical coefficents are held constant, and (2) performing in turn the same selection from within the prescribed range for each of the other variable radicals, substituents or numerical coefficents with the others being held constant. In addition to a selection made within the prescribed range for any of the variable radicals, substituents or numerical coefficents of only one of the members of the group described by the range, a plurality of compounds and compositions may be described by selecting more than one but less than all of the members of the whole group of radicals, substituents or numerical coefficents. When the selection made within the prescribed range for any of the variable radicals, substituents or numerical coefficents is a subgroup containing (i) only one of the members of the whole group described by the range, or (ii) more than one but less than all of the members of the whole group, the selected member(s) are selected by omitting those member(s) of the whole group that are not selected to form the subgroup. The compound, composition or plurality of compounds or compositions, may in such event be characterized by a definition of one or more of the variable radicals, substituents or numerical coefficents that refers to the whole group of the prescribed range for that variable but where the member(s) omitted to form the subgroup are absent from the whole group.

Other related systems, materials and methods for the removal of $CO_2$ or $SO_2$ from a gaseous mixture are disclosed in the following concurrently-filed U.S. provisional patent applications:

| | | |
|---|---|---|
| 61/313,298, 61/414,532, 61/416,421; | | 61/313,173; |
| 61/313,181; | 61/313,322; | 61/313,328; |
| 61/313,312; | 61/313,183; and | 61/313,191; | each of which is by this reference incorporated in its entirety as a part hereof for all purposes.

What is claimed is:

1. A composition as represented by the structure of the following Formula IA, Formula IIA, or Formula IIIA:

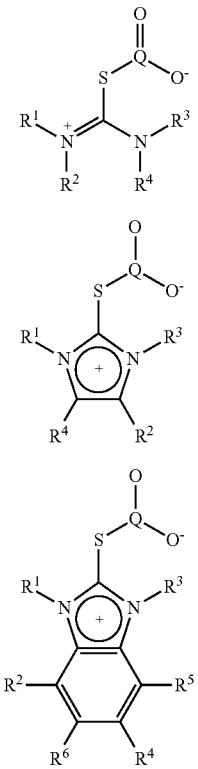

wherein
4) $R^1$, $R^2$, $R^3$, $R^4$, $R^5$, and $R^6$ are independently selected from the group consisting of:
   i) H,
   ii) halogen,
   iii) —$CH_3$, —$C_2H_5$, or $C_3$ to $C_{25}$ straight-chain, branched or cyclic alkane or alkene, optionally substituted with at least one member selected from the group consisting of Cl, Br, F, I, OH, $NH_2$ and SH;
   iv) —$CH_3$, —$C_2H_5$, or $C_3$ to $C_{25}$ straight-chain, branched or cyclic alkane or alkene comprising one to three heteroatoms selected from the group consisting of O, N, Si and S, and optionally substituted with at least one member selected from the group consisting of Cl, Br, F, I, OH, $NH_2$ and SH;
   v) $C_6$ to $C_{20}$ unsubstituted aryl, or $C_6$ to $C_{25}$ unsubstituted heteroaryl having one to three heteroatoms independently selected from the group consisting of O, N, Si and S;
   vi) $C_6$ to $C_{25}$ substituted aryl, or $C_6$ to $C_{25}$ substituted heteroaryl having one to three heteroatoms independently selected from the group consisting of O, N, Si and S; and wherein said substituted aryl or substituted heteroaryl has one to three substituents independently selected from the group consisting of:
      (A) —$CH_3$, —$C_2H_5$, or $C_3$ to $C_{25}$ straight-chain, branched or cyclic alkane or alkene, optionally substituted with at least one member selected from the group consisting of Cl, Br, F, I, OH, $NH_2$ and SH,
      (B) OH,
      (C) $NH_2$, and
      (D) SH; and
   vii) —$(CH_2)_nSi(CH_2)_mCH_3$, —$(CH_2)_nSi(CH_3)_3$, or —$(CH_2)_nOSi(CH_3)_m$, where n is independently 1-4 and m is independently 0-4;
   wherein any of $R^1$, $R^2$, $R^3$, $R^4$, $R^5$, and $R^6$ can together form a ring; and
2) Q is S or C.

2. The composition of claim 1 wherein in Formula IA $R^1$ is an aryl group, $R^2$ is an alkyl group, $R^3$ is H, and $R^4$ is an alkyl group.

3. The composition of claim 1 wherein in Formula IIA and Formula IIIA $R^1$ is an aryl group, $R^2$ is H, and $R^2$, $R^4$, $R^5$, and $R^6$ are independently H, an alkyl group, or an aryl group.

4. The composition of claim 1 wherein Q is C.

* * * * *